United States Patent
Pereira et al.

(10) Patent No.: US 6,476,254 B1
(45) Date of Patent: Nov. 5, 2002

(54) ALKOXYLATED FATTY ALCOHOL DICARBOXYLIC ACID ESTERS

(75) Inventors: Abel G. Pereira, Belleville, NJ (US); Patrick Obukowho, Fords, NJ (US)

(73) Assignee: Croda Inc., Parsippany, NJ (US)

( * ) Notice: Subject to any disclaimer, the term of this patent is extended or adjusted under 35 U.S.C. 154(b) by 0 days.

(21) Appl. No.: 09/410,585

(22) Filed: Oct. 1, 1999

Related U.S. Application Data (60) Provisional application No. 60/102,777, filed on Oct. 2, 1998.

(51) Int. Cl.[7] .................. C07C 69/66; C07C 69/34; C07C 67/00
(52) U.S. Cl. .................. 560/198; 560/182; 560/204
(58) Field of Search ................. 560/198, 182, 560/204

(56) References Cited

U.S. PATENT DOCUMENTS

| | | | |
|---|---|---|---|
| 4,061,612 A | | 12/1977 | Bertozzi et al. |
| 5,302,377 A | * | 4/1994 | Pereira et al. |
| 5,382,377 A | | 1/1995 | Raehse et al. |
| 5,455,025 A | * | 10/1995 | Pereira et al. |
| 5,597,555 A | * | 1/1997 | Pereira et al. |

* cited by examiner

*Primary Examiner*—Alan L. Rotman
*Assistant Examiner*—Taylor V. Oh
(74) *Attorney, Agent, or Firm*—Lerner, David, Littenberg, Krumholz & Mentlik, LLP (57) ABSTRACT

Fatty alkoxylated esters consisting of diesters of aliphatic or aromatic dicarboxylic acids, formed by reacting the acid with a stoichiometric excess of one or more polyalkoxylated fatty alcohols. Non-aqueous compositions for topical application are also disclosed including one or more active ingredients, and an emollient agent of the fatty alkoxylated esters of the present invention.

28 Claims, 1 Drawing Sheet

ALKOXYLATED FATTY ALCOHOL DICARBOXYLIC ACID ESTERS

The present invention claims the benefit of the United States Provisional Application No. 60/102,777 filed on Oct. 2, 1998, the disclosure of which is incorporated by reference herein.

FIELD OF THE INVENTION

The present invention relates to the field of chemical manufacture and in particular, cosmetics. It provides products having good pigment wetting and spread properties.

BACKGROUND OF THE INVENTION

Producing sunscreens and cosmetics offers a great number of challenges. Cosmetics, such as, for example, a lipstick, may require that material be easy to apply but once applied, it should not spread, smear or creep. To accomplish same, it is desirable to develop certain agents which, as additives, have a low skin spread factor. Unfortunately, it is also often necessary when making cosmetics to include pigments. The use of such pigment provides additional complications, particularly since the pigments need to be wetted. Pigment wetting agents generally have a low viscosity and tend to interfere with a low skin spread factor and complicate formulations significantly.

Fatty alkoxylated esters of aliphatic and aromatic dicarboxylic and tricarboxylic acids have been known for use in sunscreens, cosmetics and the like for their emollient properties. See U.S. Pat. Nos. 5,382,377, 5,455,025 and 5,597,555. However, while these compounds are excellent emollients and useful in formation of sunscreens, cosmetics and the like, not all of them have good pigment wetting properties, low skin spread factors, or preferably both. Ideally, additives for cosmetics and, in particular, skin products such as sunscreens, will also act as good solvents for such other additives as benzophenones. Therefore there exists a continued need for the discovery and use of various compounds which have good pigment wetting, low skin spread factors or preferably both.

SUMMARY OF THE INVENTION

These needs are met by the present invention, which provides fatty alkoxylated esters of aliphatic and aromatic dicarboxylic acids which possess exceptional pigment wetting and/or a low skin spread factor. In a particularly preferred embodiment, these compounds are also good solvents for compounds such as benzophenones. These compounds have two polyalkoxylated fatty alcohol chains covalently bonded by ester linkages to the carboxylic acid groups of aliphatic and aromatic dicarboxylic acids. See Formula I.

R1 and R2 are fatty alcohol groups and can be the same or different, and are saturated or unsaturated, substituted or unsubstituted, aliphatic of aromatic fatty groups containing from 8 to 36 carbons. X and y may both be from 0 to 40. Preferably, x and y can each be 15 but the total of x and y does not exceed 25. However, at least two alkoxy units must be present in each polyalkoxylated fatty alcohol group. A representative dicarboxylic acid is illustrated in formula I in square brackets. However, any dicarboxylic acids having between 2 to 36 carbons as described herein may be used to form the dicarboxylate esters of the present invention.

In addition, while the above Formula I illustrates all of the ethoxy units in a group and all of the propoxy units in a group, their order need not be as such. Indeed, these groups may be placed in any order, randomly, in blocks and in alternating patterns. Purely for illustrative purposes, the ethoxy units (E) and propoxy units (P) of one of the alkoxylated fatty alcohol groups may be arranged as follows: EEEP, EEPE, EPEE, PEEE, EEEPEPPPE, PEPPPEEEEPE and the like. Neither the number of E and P units, nor their orders, needs to be the same in each of the two polyalkoxylated fatty alcohols of each ester.

In a particularly preferred embodiment, x is 1 or greater and y may be 0 or greater. More preferably, the number of ethoxy units is greater than the number of propoxy units. Generally, in this embodiment, x to 40 ethoxy units are provided and 0 to 30 propoxy units are provided. Of course, since at least two alkoxy units are needed to form a polyalkoxylated fatty alcohol group, x is 1 unless the number of propoxy units is 0, in which case, x is 2. Again, x and y can each be 15 with the total of x and y not exceeding 25.

These esters possess superior properties making them suitable for use in formulating topical personal care preparations such as cosmetics, sunscreens and the like. In a particularly preferred embodiment, there is provided the composition of matter of Formula IV.

wherein B is 0 to 10 which may be saturated or unsaturated, substituted or unsubstituted, and $R_1$ and $R_2$ may be the same or different and each are fatty alcohols of 10 to 22 carbons which may be saturated or unsaturated, substituted or unsubstituted, x is 1 to 40 and y is 0 to 30 with the proviso that if y is 0, x is at least 2 and with the further proviso that x is greater than y. In a particularly preferred compound, x is 10, y is 2, B is 4 and $R_1$ and $R_2$ are each 14 carbons long and, in particular, myristyl alcohol. This compound can also be referred to as Bis ($PPG_2$, $PEG_{10}$ Myristyl) adipate. Other advantageous compounds are formed when B is 4, $R_1$ and $R_2$ are 14 to 16 carbons, x is 4 to 6 and y is 2 to 4. Again this is with the proviso that x is greater than y.

Another particularly preferred compound of the present invention is D3PA in which, in Formula IV, x is 0, y is 3, and B and $R_1$/$R_2$ are as described immediately above. Other advantageous compounds are formed where B is 4, $R_1$ and $R_2$ are 14 to 16 carbons, x is 2 to 6 and y is 2 to 6.

In accordance with another embodiment of the present invention, there is provided a fatty alkoxylated ester in which a diester of an aliphatic or aromatic dicarboxylic acid is formed by reacting the acid with a stoichiometric excess of one or more polyalkoxylated fatty alcohols.

The present invention provides fatty alkoxylated esters possessing exceptional pigment wetting properties and/or low skin spread factors both of which have long been desired by chemists for use in personal care products. Therefore, in accordance with another embodiment of the present invention, there is provided a composition for topical application including one or more active ingredients, and fatty alkoxylated ester agents of the present invention. Most preferably, the one or more active ingredients include pigments and/or sunscreening agents.

DETAILED DESCRIPTION OF THE PREFERRED EMBODIMENT

The agents of the present invention are fatty alkoxylated esters of aliphatic or aromatic, dicarboxylic acids. Aliphatic dicarboxylic acids suitable for use in the present invention contain from 2 to 36 carbon atoms. Aromatic dicarboxylic acids suitable for use in the present invention contain from 8 to 36 carbon atoms. Preferred aliphatic dicarboxylic acids contain from 3 to 8 carbon atoms. Examples of suitable aliphatic dicarboxylic acids include adipic acid, sebacic acid, malonic acid, succinic acid and maleic acid.

Preferred aromatic dicarboxylic acids contain from 8 to 12 carbon atoms. An example of a suitable aromatic dicarboxylic acid is phthalic acid. 1,2-phthalic acid, having the lowest melting point of the phthalic acid isomers, is preferred. The fatty alkoxylated esters of the present invention may be formed from, inter alia, reacting the above-described dicarboxylic acids with polyalkoxylated fatty alcohols. The polyalkoxylated fatty alcohols include a fatty alcohol group and at least two alkoxy groups. These polyalkoxylated fatty alcohols may have between about 1 and about 80 moles of the alkoxylating moieties present for each fatty alcohol moiety. They may be polyalkoxylated with, for example, polyethoxylated, polypropoxylated or both. Therefore, preferred polyalkoxylated fatty alcohols in accordance with the present invention have the structural formula of Formula II.

(II)

wherein R is either R1 or R2 and is a saturated or unsaturated, substituted or unsubstituted aliphatic or aromatic fatty moiety containing from 8 to 36, and more preferably 14 to 22 carbon atoms. Generally, a hydrogen would be bond to the terminal oxygen in the formula II to form the alcohol as described. X and y are independently zero or integers from 1 to 40, inclusive, and the sum of x and y is between 2 and 80, inclusive. In a more preferred embodiment, x is from 0 to 15, y is from 0 to 15, the total of x and y will not exceed 25 and at least 2 alkoxy groups are provided. The polyalkoxylated fatty alcohol depicted above is prepared by the polyalkoxylation of a saturated or unsaturated, substituted or unsubstituted, aliphatic or aromatic fatty alcohol having the structural formula of Formula III.

R—OH    III where R is as defined herein.

As is well understood by those of ordinary skill in the art, fatty alcohols are derived from fatty acids, and for this reason, groups such as R are defined as fatty moieties. Fatty alcohols are often commercially prepared from a mixture of fatty acids and contain a mixture of fatty moieties. Therefore, in accordance with the present invention, R for each polyalkoxylated fatty alcohol chain may be the same or different.

Saturated, unsubstituted, aliphatic fatty moieties containing from 8 to 36 carbon atoms are preferred, and such fatty moieties containing from 10 to 16 carbon atoms are even more preferred. The myristyl fatty moiety containing 14 carbon atoms is most preferred. For diesters of dicarboxylic acids, aliphatic fatty moieties containing from 10 to 22 carbon atoms are suitable for use with the present invention. Diesters of dicarboxylic acids with ethoxylated 6-carbon alcohols are disclosed by U.S. Pat. No. 4,061,612 as being useful as plasticizers with extended temperature ranges in elastomers. This is attributable to the short 6-carbon alcohol chains, which provide a low molecular weight diester with low viscosity that consequently has the solvent properties required of a plasticizer.

But even more important than the absolute number of ethoxy and propoxy units is their effect. It has been found that polyalkoxylated fatty alcohol esters of dicarboxylic acids can be produced which have properties not common to the class. Certain of these compounds have a skin spread factor of less than 8 or a viscosity of less then 19,000 cps. More preferably, the composition of matter will exhibit both low spread factor and viscosity. The discovery that some compounds of this class can exhibit these advantageous properties is one particularly important aspect of the present invention.

The compounds with these properties can include all ethoxy groups, all propoxy groups or a mixture of each. While not intended to be a hard and fast limitation, compounds exhibiting these properties generally have no more than a total of 80 alkoxy groups in each polyalkoxylated fatty alcohol group. More preferably, the number of alkoxy groups is 40 or less.

It has also been found that when the polyalkoxylated fatty alcohols include more ethoxy groups than propoxy groups, the resulting dicarboxylic acid esters can also have improved solubility for certain cosmetic additives such as benzophenones. The compound Bis (PPG$_2$, PEG$_{10}$ Myristyl) adipate has a viscosity of 18,000 cps, a spread factor of 2.9 and can solubilize at least 20% by weight of benzophenone 3 forming a clear solution even after 48 hours.

The 8 to 36 and preferably 10 to 22 carbon chain length fatty alkoxylated diesters of dicarboxylic acids of the present invention have high molecular weights and viscosities, and lack the solvent properties to function effectively as a plasticizer. Instead, the higher molecular weight and viscosity results in a diester having desirable emollient properties. Such emollient properties cannot be obtained from the lower molecular weight low viscosity diesters disclosed by U.S. Pat. No. 4,061,612. Saturated, unsubstituted aliphatic moieties are preferred for the diesters of dicarboxylic acids of the present invention, and such fatty moieties containing from 14 to 18 carbon atoms are more preferred. Even more preferred are fatty moieties containing from 14 to 16 carbon atoms. As previously noted, the myristyl fatty moiety containing 14 carbon atoms is particularly preferred.

In the above-depicted polyalkoxylated fatty alcohol of Formula II, x and y can be, collectively selected from integers from 2 to 80, inclusive, and independently selected from integers from 0 to 40, inclusive. Even more preferably, x is 0 to 15, y is 0 to 15 and the total of x and y will not exceed 25. More preferably, x and y may each be up to 40 with the proviso that at least two alkoxy units are provided. In a particularly preferred aspect of the present invention, x can be 1 to 40 and y can be 0 to 30. In this case, if y is 0, x must be at least 2. It is also preferred in this case that the number of ethoxy units be greater than the number of propoxy units, if any. Of course, it is possible that one polyalkoxylated fatty alcohol group will have 80 alkoxy units while the other group actually had additional alkoxy groups, so long as the resulting compound has the advantages of this invention.

As will be readily appreciated by those of ordinary skill in the art, the dicarboxylic acid-based esters of the present invention will be esterified on both carboxylic acid groups by the above-depicted polyalkoxylated fatty alcohols. Of course, different fatty alcohols may be attached to the same dicarboxylic acid. The sum of all x's and y's in every polyalkoxylated fatty alcohol chain of Formula I should not exceed 200. The sum of all x's and y's preferably do not exceed 160, and more preferably do not exceed 80.

With respect to Formula IV, in one preferred embodiment, when the alcohol is a myristyl moiety, x is preferably zero and each y is preferably an integer independently selected from 2 to 40, inclusive. These compounds have exceptional viscosity, pigment wetting and spread factors. A particularly preferred example is DP3A in which, in Formula IV, $R_1$ and $R_2$ are myristyl, B is 4, x is 0 and y is 3. Again with respect to Formula IV in another preferred embodiment, the fatty alcohol is myristyl, B is 4, x is preferably 1 to 40 and y may be 0 to 30. When y is 0, x is at least 2. In one particularly desirable compound, x is 10 and y is 2.

The fatty alkoxylated esters of the invention described above are prepared by initially reacting, either sequentially, or in their mixed forms, saturated or unsaturated, substituted or unsubstituted, aliphatic or aromatic fatty alcohols containing from 8 to 36 carbon atoms, with an epoxide, preferably ethylene oxide, propylene oxide, or mixtures thereof, in the presence of an acidic or basic catalyst. It is typical of propylene oxide to branch upon opening of the epoxide ring. This branching tends to impart liquidity to the compound. Catalysts suitable for this reaction are well-known in the art and include, for example, inorganic alkalis such as alkali metal oxides and hydroxides, e.g., potassium hydroxide, sodium methoxide, sodium borohydride, protic and Lewis acids, e.g., boron trifluoride, stannic chloride and sulfuric acid. Amines, quaternary ammonium compounds, water and other acids may also be employed. Mixtures of catalysts may also be employed. Certain reactive substrates known in the art, for example, acetylenic alkanols, may eliminate the need for such catalysts. Inorganic catalysts such as Tin catalysts can also be used.

Preferably, a basic catalyst is used in this reaction and most preferably from about 0.1 to about 2.0 weight percent of potassium or sodium hydroxide, sodium methoxide, sodium borohydride or mixtures thereof, based on the weight of the alcohol. The reaction is carried out under anhydrous conditions to avoid formation of by-products, and at a temperature which is, preferably, in the range of from about 110° C. to about 200° C., although higher temperatures may be utilized. The reaction can be carried out at substantially atmospheric pressure, although it is preferably carried out in an autoclave at pressures of from about 10 psig to about 80 psig. The amount of ethylene oxide or propylene oxide introduced to the reaction zone, and the duration of reaction time, determines the number of moles of such components added to the fatty moiety, R, of the fatty alcohol.

In Formula I, x represents the number of moles of ethylene oxide which are incorporated into each polyalkoxylate fatty alcohol chain. Likewise, y represents the number of moles of propylene oxide that are incorporated into the polyalkoxylated fatty alcohol chain. As will be readily appreciated by those of ordinary skill in the art, stoichiometric quantities of fatty alcohols, ethylene oxide and propylene oxide are reacted together, and stoichiometric quantities of the polyalkoxylated fatty alcohol and dicarboxylic acid are reacted together. Preferably, the reaction is carried out sequentially in that the fatty alcohol is first reacted with the propylene oxide and after complete reaction, the ethylene oxide is introduced into the reaction. After complete reaction of the ethylene oxide, an acid, e.g., phosphoric acid or acetic acid, is introduced into the reaction mixture to neutralize the basic catalyst. The resulting polyalkoxylated fatty alcohol is then reacted with a suitable dicarboxylic acid. Examples of suitable acids were listed above.

A conventional esterification reaction of the acid with the polyalkoxylated fatty alcohol is carried out. This may be accomplished with or without catalyst. Preferred catalysts are methane sulfonic acid and para-toluene sulfonic acid. The esterification is typically performed by combining stoichiometric quantities of the polyalkoxylated fatty alcohol and the acid to be esterified. As is well understood by those of ordinary skill in the art, when two polyalkoxylated fatty alcohol chains are to be added to the acid, the polyalkoxylated fatty alcohol and acid to be esterified should be combined in a molar ratio of 2:1. However, a slight stoichiometric excess should be employed to insure complete esterification and a low acidity. The polyalkoxylated fatty alcohol is a liquid, therefore a reaction solvent is not needed. Of course, known solvents can be employed if desired.

The polyalkoxylated fatty alcohol, acid and catalyst are combined with mixing to form a reaction mixture. The reaction mixture is heated with mixing at a temperature between about 155° C. and about 250° C., and preferably at a temperature between about 170° C. and 220° C. until an acid value of less than 8 mg KOH, and preferably less than 5 mg KOH is obtained. The reaction mixture is then cooled below 85° C. and washed with water, preferably without neutralizing the catalyst. Higher temperatures should be avoided to prevent loss of the polyalkoxylated fatty alcohols and, consequently, incomplete esterification and higher than desired acidity. The ester layer is separated and heated under vacuum until a moisture content of less than 0.2 percent is obtained.

As noted above, the polyalkoxylated fatty alcohols can be prepared by reacting mixed forms of fatty alcohols containing from 8 to 36 carbon atoms with mixtures of ethylene oxide and propylene oxide. Therefore, the resulting polyalkoxylated fatty alcohol can contain a mixture derived from the ethoxylation and the propoxylation of mixtures of fatty alcohols containing from 8 to 36 carbon atoms.

Aqueous topical preparations in accordance with the present invention include the agent of the present invention and one or more active ingredients, with the balance being water. As mentioned above, a separate emollient agent of mineral oil, petrolatum and the like can also be included. However, the compounds of the present invention have emollient properties. Suitable active agents for use in such topical preparations include sunscreens, pigments, moisturizers, film formers, detergents, thickening agents, emulsifiers, antiseptic agents, conditioning agents, and deodorant actives.

The topical preparations of the present invention, in addition to including the compositions of the present invention, one or more active ingredients, water and the optional emollient agent, may also include excipients such as fragrances, proteins, humectants, salts, preservatives, essential oils and the like. These additional components may be added in various amounts as is well-known in the cosmetic formulation art.

Typical aqueous topical preparations in accordance with the present invention include the dicarboxylic acid esters of the present invention, in a range of from about 0.20 to about 40.0 percent by weight of the composition, preferably from about 3.0 to about 20.0 percent by weight of the composition. The one or more active ingredients may be present in an amount from about 0.20 to about 40.0 percent by weight of the composition, preferably from about 3.0 to about 20.0 percent by weight of the composition. When used, the additional emollient is blended with the agents of the present invention in a ratio of about 10:1 to 1:10 parts ester agent of the present invention. The balance is generally excipients and water or some aqueous solvent system.

Non-aqueous topical preparations in accordance with the present invention may also be prepared. Such preparations include the agents of the present invention and one or more of the above-listed active ingredients. An emollient agent of mineral oil, petrolatum, and the like may again optionally be included, as may the above-described excipients fragrances, proteins, humectants, salts, preservatives, essential oils and the like.

Typical non-aqueous topical preparations in accordance with the present invention include the agents of the present invention, in a range of from about 0.20 to about 99.0 percent by weight of the composition, preferably from about 10 to about 90.0 percent by weight of the composition, and more preferably from about 25 to about 75 percent by weight of the composition. The one or more active ingredients may be present in an amount from about 0.20 to about 99.0 percent by weight of the composition, preferably from about 10 to about 90.0 percent by weight of the composition, and more preferably from about 25 to about 75 percent by weight of the composition.

As with the aqueous topical preparations, the emollient agent, when present, may be blended with the agents of the present invention in a ratio of about 10:1 to about 1:10 parts ester agent of the invention.

The polyalkoxylated fatty alcohol esters of dicarboxylic acids of the present invention (also sometimes referenced as fatty polyalkoxylated fatty alcohol esters of dicarboxylic acids) are particularly useful in ways not previously appreciated. While a broad class of these compounds were found to be useful as emollients, See U.S. Pat. Nos. 5,302,377, 5,455,025 and 5,597,555, the texts of which are hereby incorporated by reference, it has been found that the polyalkoxylated fatty alcohol dicarboxylic acid esters of the present invention are particularly useful in topical formulations where a low skin spread factor and/or good pigment wetting is desirable.

The skin spread factor is determined by applying, for example, 5 microliters of a product to a 3.14 cm diameter circle on the volar surface of the forearm. The product is spread evenly within the circle and allowed to spread for a fifteen minute period. The test site and surrounding area of the forearm is then sprayed with a 1 percent solution of FD&C Blue No. 1. The area not stained by the blue dye indicates the area onto which the product spread. The skin spread factor is obtained by dividing the resulting area by the initial area. In accordance with the present invention, formulations have a skin spread factor of less than about 8, preferably less than about 5.

Pigment wetting properties are determined by preparing a dye slurry and measuring viscosity. For example, a slurry can be prepared using an alkoxylated fatty alcohol dicarboxylic acid ester of the present invention mixed with 35 percent mica or any dye. The viscosity of the slurry is determined after allowing the slurry to stand for five minutes. The lower the viscosity, the better the pigment wetting properties of the ester. Desirably, in accordance with the present invention, viscosity of the resulting dye slurry will be below about 20,000 cps, preferably between about 500 and 15,000 cps and most preferably between about 500 and 5,000 cps based on a 65% ester, 35% pigment mixture (measured in weight percent). Viscosity will vary if a different testing mixture is used.

Figure 1A:
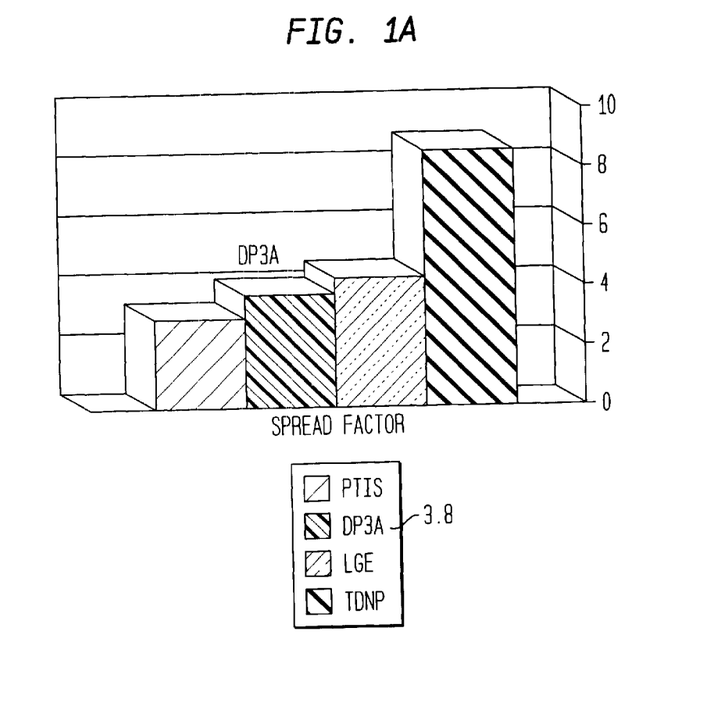
FIG. 1A illustrates the skin spread factor for an ester agent (DP3A) of the present invention.
Figure 1B:
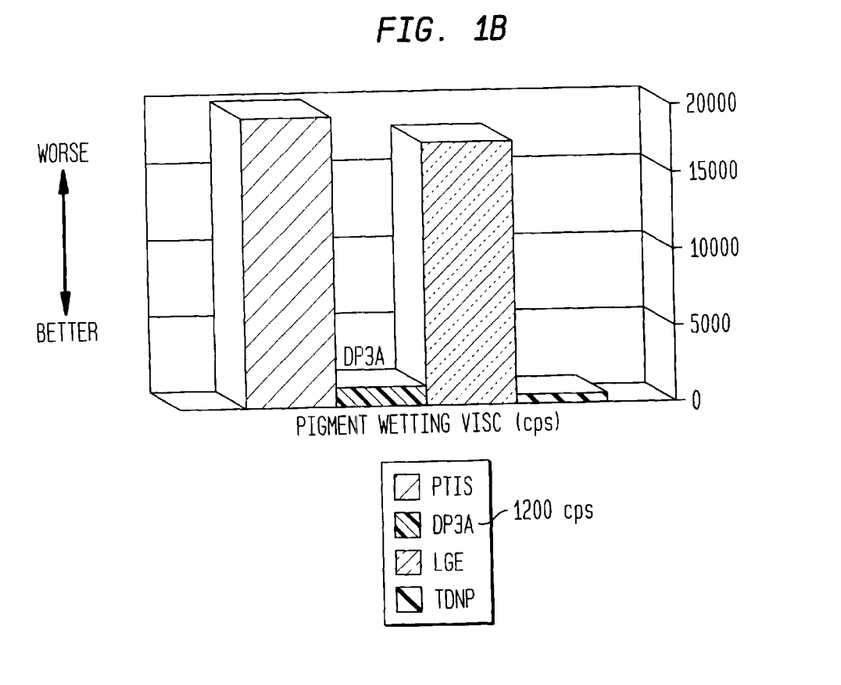
FIG. 1B illustrates the pigment wetting of an ester agent (DP3A) of the present invention.

The low spreading properties of the esters of the present invention allow them to form thicker, more uniform films on the skin. This is desirable for obtaining, for example, sunscreen formulations with a high resistance to wash off and a high SPF value. In make-up, the low skin spread factor enables the production of make up which stays in place once it is applied. Feathering, creeping, or smearing are greatly reduced or eliminated. As shown in FIG. 1A, the skin spread factor of DP3A (Di-PPG-3 Myristyl Ether Adipate) is about 3.8. Thus, it is superior to TDNP (Tridecyl Neopentanoate, first column from the right); LGE (Lignoceryl Erucate, second column from the right) but not as good as PTIS (Pentaerythrityl Tetraisostearate, first column from the left). On the other hand, as shown in FIG. 1B, DP3A has a viscosity of about 1200 cps. DP3A is illustrated in the second column from the left. PTIS is shown in the first column from the left and has a much higher viscosity of close to 20,000 cps. LGE, second column from the right also has a relatively high viscosity in excess of 15,000 cps. TDNP, first column from the right, is the least viscous material, having a viscosity of under 1000 cps.

The contrast is perhaps the most interesting. something that has a low skin spread factor would, presumably, be very viscous and hard to spread. PTIS, for example, has a very high viscosity and a very low skin spread factor. In contrast, TDNP has a very high skin spread factor meaning it is relatively easily spread and a relatively low viscosity. This would seem to be consistent. LGE has a relatively low skin spread factor, it has a relatively high viscosity. Surprisingly, compounds in accordance with the present invention, such as DP3A, have a relatively low skin spread factor and yet a relatively low viscosity meaning they are capable of significant pigment wetting and will not spread undesirably.

The good pigment wetting properties of these esters make them ideal for use in sunscreens containing pigments such as zinc oxide or titanium dioxide, make up and other systems containing inorganic or organic pigments. The pigment wetting properties of the esters enable them to surround the pigment particles and keep them suspended. This prevents the pigment particles from glomerulating and forming a viscous mass. Good pigment wetting also promotes uniform distribution of the pigment in the formulation, even during shelf storage as well as uniform distribution on the skin.

EXAMPLES

Example 1

Preparation of PPG 3 Myristyl Ether

Propylene oxide was bubbled into 685 g of myristyl alcohol in the presence of potassium hydroxide catalyst until three moles of propylene oxide were added per mole of myristyl alcohol, thus obtaining a pale, yellow liquid (PPG 3 myristyl ether) as the major product.

Example 2
Preparation of DI-PPG-3 Myristyl Maleate

A four-necked flask was charged with 906 g of the PPG-3 myristyl ether of Example 1 and 94 g of maleic anhydride. A catalytic amount of methane sulfonic acid was added and the reaction mixture was heated at 120° C. until an acid value of less than 8 mg KOH was obtained. The product was cooled to 85° C. and washed with water. The ester layer was separated and heated under vacuum until a moisture content of less than 0.2 percent was obtained. Filter clay was added and the product was vacuum filtered, yielding di-PPG-3 myristyl maleate, a clear, pale yellow liquid.

Example 3

DP3A provides low spreading and high pigment wetting, making it ideal as the solvent and pigment dispersant for a sunscreen cream. CRODAFOS N-3 NEUTRAL is used to neutralize the positive charges (i.e., charge density) on the zinc oxide and titanium dioxide, making these inorganic pigments more dispersible and easier to formulate.

| Ingredients | % |
|---|---|
| Part A | |
| DP3A (Di-PPG-3 Myristyl Ether Adipate) | 10.0 |
| CRODAFOS N-3 NEUTRAL (DEA Oleth-3 Phosphate) | 0.5 |
| Zinc Oxide (1) | 3.0 |
| Titanium Dioxide (2) | 2.0 |
| Part B | |
| VOLPO S-10 (Steareth-10) | 1.0 |
| CRODAFOS CES (Cetearyl Alcohol (and) Dicetyl Phosphate (and) Ceteth-10 Phosphate) | 4.0 |
| Part C | |
| Deoionized Water | 78.1 |
| Citric Acid Solution (10%) | 0.4 |
| Part D | |
| Propylene Clycol (and) Diazolidinyl Urea (and) Methyl Paraben (and) Propyl Paraben (3) | 1.0 | pH = 6.0 + 0.5
Viscosity = 16,000 cps + 10% (RVT, TC Spindle, 10 RPM @ 25° C.)

Procedure

Combine first two ingredients of Part A with mixing and heat to 50° C. Maintain temperature and slowly add zinc oxide and then titanium dioxide, mixing well after each addition. When uniform add the ingredients from Part B and heat to 70° C. with mixing. Combine ingredients in Part C, heat to 70° C. and slowly add to the Part A/B mixture. Continue mixing and cool to 65° C. Remove propeller mixer, insert homomixer and process batch to 60° C. Resume propeller mixing and cool to 45° C. Add Part D with mixing and cool to desired fill temperature.

1) Z-Cote (Sunsmart Inc.)
2) T-Cote (Sunsmart Inc.)
3) Germaben II (ISP/Sutton Labs)

Example 4

This simple formula offers the economy and convenience of single phase production, yet produces a lotion with the elegant emollience of an upscale product. DP3A is a novel de-ester that provides the lotion with an exceptionally lubricious skin feel, excellent rub-in, low skin spread factor and good pigment wetting.

| Ingredients | % |
|---|---|
| Part A | |
| Deionized Water | 77.0 |
| DP3A (Di-PPG-3 Myristyl Ether Adipate) | 10.0 |
| INCROQUAT BEHENYL TMS (Behentrimonium Methosulfate (and) Cetearyl Alcohol) | 5.0 |
| Glycerin | 5.0 |
| Part B | |
| Cyclomethicone (1) | 2.0 |
| Propylene Glycol (and) Diazolidinyl Urea (and) Methyl Paraben (and) Propyl Paraben (2) (preservative, Germaben II) | 1.0 | pH = 4.4 + 0.5
Viscosity = 11,000 cps (RVT Spindle #TC @ 10 rpm)
(1) Dow Corning 345 Fluid (Dow Coming)
(2) Germaben II (ISP/Sutton Labs)

Procedure

Combine ingredients of Part A with mixing and heat to 70–75° C. Cool with mixing to 50° C. and add ingredients of Part B individually. Continue mixing and cool to desired fill temperature. The result is a moisturizing lotion which could be formulated into a hair of skin product.

Example 5

A typical sunscreen formula containing Bis (PPG-2, PEG-10 Myristyl Alcohol) Adipate is as follows:

| | % W/W |
|---|---|
| Crodafos CES (Cetearyl Alcohol (and) Dicetyl Phosphate (and) Ceteth-10 Phosphate) | 10.00 |
| Bis (PPG-2, PEG-10 Myristyl Alcohol) Adipate | 25.00 |
| Benzophenone 3 | 5.00 |
| Germaben II (preservative) | 1.00 |
| Water | 59.00 |
| Potassium Hydroxide | 0.25 |

Procedure

The adipate and benzophenone are combined and heated to 70° C. with stirring, the Crodafos CES is next added with continued heating and stirring. Water is next added and heating is continued with stirring for about 5 minutes. The mixture is cooled to about 30° C.–35° C. The remaining ingredients are then added and mixing continued for at least about one hour as the mixture cools to room temperature.

What is claimed is:

1. A fatty alkoxylated ester of dicarboxylic acid having the formula where is a dicarboxylic group of said dicarboxylic acid, B includes from 4 to 12 carbon atoms, x is greater than y, and the sum of x and y is greater than 2; $R_1$ and $R_2$, same or different, are each a fatty all group, and wherein said fatty alkoxylated ester has a skin spread far of less than about 8 or a viscosity of less than 19,000 cps.

2. The fatty alkoxylated ester of claim 1, wherein $R_1$ and $R_2$ contain from 8 to 36 carbon atoms.

3. The fatty alkoxylated ester of claim 2, wherein $R_1$ and $R_2$ each contain from 10 to 22 carbon atoms.

4. The fatty alkoxylated ester of claim 3, wherein $R_1$ and $R_2$ are each a myristyl fatty group.

5. The fatty alkoxylated ester of claim 1, wherein said dicarboxylic acid is selected from the group consisting of adipic and phthalic.

6. A composition of matter having the formula wherein B includes 4 to 12 carbon atoms, saturated or unsaturated, substituted or unsubstituted, and $R_1$ and $R_2$ may be the same or different and each are fatty alcohols of 10 to 22 carbons, saturated or unsaturated, substituted or substituted; x is 1 to 40 and y is 0 to 30 with the proviso that if y is 0, x is at least 2 and with the further proviso that x is greater than y and the sum of x and y is greater than 2.

7. The composition of matter of claim 6 wherein x is 10, y is 2, B is 4 and $R_1$ and $R_2$ are each 14 carbons.

8. A composition of matter having the formula wherein B includes 4 carbon atoms, $R_1$ and $R_2$ are each 14 carbons in length, x is 0 and y is 3.

9. An aqueous topical preparation comprising between about 0.20 and about 40.0 percent by weight of an active ingredient, between about 0.20 and about 40.0 percent of an fatty alkoxylated ester of a dicarboxylic acid having the formula wherein is a dicarboxylic group of said dicarboxylic acid, B includes 4 to 12 carbon atoms, the sum of x and y is greater than 2 and x is greater than y, with the proviso that if B is 4, x is 0 and y is 3; $R_1$ and $R_2$, same or different, are each a fatty alkyl group; said fatty alkoxylated ester having a skin spread factor of less then about 8 and a viscosity of less than 19,000 cps.

10. The aqueous topical preparation of claim 9, wherein x varies from 1 to 40 and y varies from 1 to 40, with the proviso that if y is 0, x is 2.

11. The aqueous topical preparation of claim 9, wherein x varies from 1 to 40 and y varies from 1 to 30, with the proviso that if y is 0, x is 2.

12. The aqueous topical preparation of claim 10 or 11 wherein said active agent is a sunscreen, pigment, moisturizer, film former, detergent, thickening agent, emulsifier, antiseptic agent, conditioner or deodorant.

13. The aqueous topical preparation of claim 10 or 11 wherein said active agent and said fatty alkoxylated ester of a dicarboxylic acid range from about 3 to about percent by weight respectively.

14. A non-aqueous topical preparation comprising between about 0.20 ad 99.0 percent by weight of an active ingredient and 0.20 to about 99.0 percent by weight of a fatly alkoxylated ester of a dicarboxylic acid having the formula wherein is a dicarboxylic group of said dicarboxylic acid, B includes 4 to 12 carbon atoms, the sum of x and y is greater than 2 and x is greater than y, with the proviso hat if B is 4, x is 0 and y is 3; $R_1$ and $R_2$, same or different, are each a fay alkyl group, said fatty alkoxylated ester having a skin spread factor of less than 8 and a viscosity of less than 19,000 cps.

15. The non-aqueous topical preparation of claim 14, wherein x varies from 0 to 40 and y varies from 0 to 40.

16. The non-aqueous topical preparation of claim 14, wherein x varies from 1 to 40 and y varies from 1 to 30, with the proviso that if y is 0, x is 2.

17. The non-aqueous topical preparation of claim 15 or 16 wherein said active agent is a sunscreen, pigment, moisturizer, film former, detergent, thickening agent, emulsifier, antiseptic agent, conditioner or deodorant.

18. The non-aqueous topical preparation of claim 15 or 16 wherein said active agent and said fatty alkoxylated ester of a dicarboxylic acid range from about 25 to about 75 percent by weight respectively.

19. A composition of matter having the formula wherein B includes 4 to 12 carbon atoms, saturated or unsaturated, substituted or unsubstituted, and $R_1$ and $R_2$ may be the same or different and each are fatty alcohols of 14 to 16 carbons which may be saturated or unsaturated, substituted or unsubstituted, x is 2 to 6 and y is 2 to 6.

20. The composition of matter of claim 19 wherein x is 4 to 6 and y is 2 to 4.

21. The composition of matter of claim 19 wherein x is 4 to 6 and y is 2 to 4 and wherein x is greater than y.

22. The fatty alkoxylated ester of claim 1, wherein x is 4 to 6, and y is 2 to 4.

23. The fatty alkoxylated ester of claim 1, wherein x is 2, and y is 0.

24. The fatty alkoxylated ester of claim 1, wherein said dicarboxylic group has 10 carbons or less, said dicarboxylic acid being saturated or unsaturated, substituted or unsubstituted.

25. A fatty alkoxylated ester of dicarboxylic acid having the formula wherein B includes 4 carbon atoms, the sum of x and y is greater than 2, and $R_1$ and $R_2$, same or different, is a fatty alkyl group, said fatty alkoxylated ester having a skin spread factor of less than about 8 or a viscosity of less than 19,000 cps.

26. The fatty alkoxylated ester of claim 1 or 25, wherein x is from 0 to 40, and y is from 0 to 30.

27. The fatty alkoxylated ester of claim 1 or 25, wherein x is from 0 to 15, and y is from 0 to 15, and the sum of x and y does not exceed 25.

28. The fatty alkoxylated ester of claim 1 or 25, wherein $R_1$ and $R_2$ each have 14 to 16 carbon atoms.

* * * * *

UNITED STATES PATENT AND TRADEMARK OFFICE
CERTIFICATE OF CORRECTION

PATENT NO. : 6,476,254 B1  Page 1 of 1
DATED : November 5, 2002
INVENTOR(S) : Abel G. Pereira and Patrick Obukowho It is certified that error appears in the above-identified patent and that said Letters Patent is hereby corrected as shown below:

Column 8,
Line 37, "something" should read -- Something --.

Column 11,
Line 11, "all" should read -- alkyl --.
Line 13, "far" should read -- factor --.

Column 12,
Line 35, insert -- 30 -- after "about" (second occurrence).
Line 39, "fatly" should read -- fatty --.
Line 59, "hat" should read -- that --.
Line 60, "fay" should read -- fatty --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,476,254 B1
DATED : November 5, 2002
INVENTOR(S) : Abel G. Pereira and Patrick Obukowho It is certified that error appears in the above-identified patent and that said Letters Patent is hereby corrected as shown below:

Column 8,
Line 37, "something" should read -- Something --.

Column 11,
Line 11, "all" should read -- alkyl --.
Line 13, "far" should read -- factor --.

Column 12,
Line 35, insert -- 30 -- after "about" (second occurrence).
Line 39, "fatly" should read -- fatty --.
Line 59, "hat" should read -- that --.
Line 60, "fay" should read -- fatty --.

Signed and Sealed this

Twenty-ninth Day of June, 2004

JON W. DUDAS
*Acting Director of the United States Patent and Trademark Office*